United States Patent [19]

Zhang et al.

[11] Patent Number: 5,853,704
[45] Date of Patent: Dec. 29, 1998

[54] FLUORIDE DENTIFRICES OF ENHANCED EFFICACY

[75] Inventors: Yun Po Zhang, Hillsborough; Abdul Gaffar, Princeton, both of N.J.

[73] Assignee: Colgate-Palmolive Company, New York, N.Y.

[21] Appl. No.: 935,367

[22] Filed: Sep. 22, 1997

[51] Int. Cl.⁶ .............................. A61K 7/16; A61K 7/18
[52] U.S. Cl. .................................. 424/52; 424/49
[58] Field of Search ........................... 424/49–58

[56] References Cited

U.S. PATENT DOCUMENTS

| | | | |
|---|---|---|---|
| 4,487,757 | 12/1984 | Kiozpeoplou | 424/49 |
| 4,687,663 | 8/1987 | Schaeffer | 424/52 |
| 4,992,420 | 2/1991 | Neeser | 424/49 |
| 4,994,441 | 2/1991 | Neeser | 424/49 |
| 5,075,424 | 12/1991 | Tanimoto et al. | |
| 5,216,129 | 6/1993 | Berrocal et al. | 530/360 |
| 5,227,154 | 7/1993 | Reynolds | 424/49 |
| 5,427,769 | 6/1995 | Berrocal et al. | 424/49 |

*Primary Examiner*—Shep K. Rose
*Attorney, Agent, or Firm*—Henry S. Goldfine

[57] ABSTRACT

A multicomponent anticaries dentifrice composition and method of use therefore, having a first dentifrice component containing a fluoride ion source and a second dentifrice component containing a casein glycomacropeptide compound, wherein the components are physically separated before use and are combined immediately prior to application to the teeth, the dentifrice exhibiting enhanced enamel remineralization.

14 Claims, No Drawings

FLUORIDE DENTIFRICES OF ENHANCED EFFICACY

BACKGROUND OF THE INVENTION

1. Field of the Invention

The present invention relates to a multicomponent anticaries dentifrice composition and method of use therefore, having a first component containing a fluoride ion source, and a second component containing a casein glycomacropeptide and, more particularly, to such a composition which exhibits enhanced anticaries and remineralization efficacy over like dentifrice compositions containing fluoride alone.

2. The Prior Art

It is known that dental caries are caused by the production of acid by certain specific bacteria, such as streptococcus mutans. Repeated cycles of such acid attack results in microscopic demineralization or decalcification of the hydroxyapatite structure of the tooth enamel and the formation of an incipient carious lesion. However, saliva provides a continuing source of calcium and phosphate to the tooth enamel which tends to remineralize the hydroxyapatite structure of the enamel, inhibiting and reversing the demineralizing carious process.

Casein glycomacropeptides (hereinafter "CGMP"), which are natural ingredients of lactic origin, have been identified by the art to be effective antibacterial agents against microorganisms responsible for dental plaque and caries when applied to the tooth and periodontium, which is the investing and supporting tissue surrounding the tooth (i.e. the periodontal ligament, the gingiva, and the alveolar bone). For example, U.S. Pat. Nos. 4,992,420 and 4,994,441 disclose that casein phosphopeptides derived from kappa-casein are effective for inhibiting the growth of streptococcus mutans, a bacteria species associated with dental caries and plaque formation. However, in vivo human testing has shown that such CGMP agents, at concentrations of 5% by weight, are over 20% less effective than the 1100 ppm fluoride ion as NaF generally available within commercial dentifrices.

It has long been known that fluoride-providing compounds are safe and effective anticaries agents which promote the remineralization process. However, generally the maximum amount of fluoride ion approved by the U.S. Food and Drug Administration (FDA) for use in over-the-counter dentifrice formulations is limited to 1150 ppm. Further, efforts to incorporate in fluoride containing dentifrices such natural ingredients as CGMP to enhance the anticaries efficacy of the fluoride have been stymied, as CGMP has been found to be incompatible with sources of fluoride ions, such as sodium fluoride, sodium monofluorophosphate, potassium fluoride and the like; as the efficacy of the combined CGMP and fluoride ion sources are deactivated.

There is a clear need in the art to prepare dentifrices having improved remineralization and resultant anticaries efficacy over the FDA approved fluoride ion concentration, with natural ingredients such as CGMP, without any inactivation of the desired beneficial properties of the fluoride or the CGMP.

SUMMARY OF THE INVENTION

The present invention encompasses a composition and method of enhancing the remineralization and resultant anticaries efficacy of fluoride dentifrices, comprising the application to the tooth of a multicomponent dentifrice composition, having a first dentifrice component containing a fluoride ion releasing compound and a second dentifrice component containing a casein glycomacropeptide compound; the first and second components being separated prior to use and when combined, upon application to the teeth, the dentifrice provides unexpectedly, significantly enhanced enamel remineralization and over that of either component independently, as will be hereinafter demonstrated.

DESCRIPTION OF THE PREFERRED EMBODIMENTS

In use, the components of the multicomponent dentifrice of the present invention comprise a first fluoride ion releasing compound containing dentifrice component, and a second casein glycomacropeptide containing dentifrice component which may conveniently be combined in approximately equal weight proportions, so that only about one-half of the concentration of any particular ingredient within either component will be present when the components are combined and applied to the teeth, as by brushing. The formulations for each component provides rheological characteristics so that each component is delivered in the desired predetermined amount, by extrusion from a dual compartmented tube or pump device.

Dentifrice Vehicle Common to Each Component

In the preparation of dentifrice components of the present invention, the respective fluoride ion releasing compound or casein glycomacropeptide containing compound is incorporated within a dentifrice vehicle suitable for use in the oral cavity, which contains water, humectant, surface active agent and a polishing agent or abrasive. The humectant is generally a mixture of humectants, such as glycerol, sorbitol and polyethylene glycol of a molecular weight in the range of 200–1000, but other mixtures of humectants and single humectants may also be employed. The humectant content within each of the two components is in the range about of 15% to about 40% by weight and preferably about 20 to about 30% by weight. The water content is from about 30% to about 60%, and preferably about 45% by weight.

In the present invention, the surface active agent aids in the thorough dispersion of the dentifrice throughout the oral cavity when applied thereto, as well as, improve the dentifrice's cosmetic acceptability and the foaming properties. Surface active agents which can be included within the vehicle of each of the dentifrice components of the present invention, include anionic, nonionic or ampholytic compounds; anionic compounds being preferred. Examples of suitable surfactants include salts of the higher alkyl sulfates, such as sodium lauryl sulfate or other suitable alkyl sulfates having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristyol- and N-palmitoyl sarcosinates; salts of the esters of such fatty acids with isotonic acid or with glycerol monosulfate, such as the sodium salt of monosulfated monoglyceride of hydrogenated coconut oil fatty acids; salts of olefin sulfonates, e.g. alkene sulfonates or alkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium, potassium or mono-, di or triethanol amine.

The quantity of surface active agent present within the various components of the present invention totals from about 0.5 to about 3.0% by weight, preferably about 0.8 to about 2.5% by weight of the combined multiple components.

Polishing agents or abrasives which may be incorporated in the dentifrice vehicle of each component, include sodium metaphosphate, potassium metaphosphate, tricalcium phosphate, dihydrated dicalcium phosphate, aluminum silicate, calcined alumina, bentonite or siliceous materials or combinations thereof. However, generally these materials are interactive with CGMP and should not be included in the CGMP dentifrice component. An exception is siliceous materials, which are not interactive with CGMP and therefore may be formulated in any of the dentifrice components. A preferred siliceous polishing agent is a silica having a mean particle size up to about 20 microns; including a precipitated amorphous hydrated silica available under the trademark of Zeodent 115, from J. M. Huber Chemicals Division, Havre de Grace, Md. 21078, or available under the trademark of Sylodent 783 from Grace Davidson, Baltimore, Md. 21203.

To maintain comparable rheological characteristics between the different dentifrice components of the instant invention, it is preferred to have the polishing agent in generally comparable quantities in each of the components. Accordingly, as stated above, a siliceous polishing agent which will not interact with CGMP is preferred in each component of the present invention, at a concentration from about 10 to about 30% by weight, and preferably 15 to about 25% by weight of each component.

Fluoride Containing Dentifrice Component

The first, fluoride ion containing dentifrice component contains a water-soluble fluoride compound as a source for releasing fluoride ions. The fluoride compound may be in an amount sufficient to release a fluoride ion concentration in the composition at 25° C., and/or when it is used, from about 0.025% (or 250 ppm) to about 1% by weight (or 10,000 ppm), preferably from about 0.04% (or 400 ppm) to about 0.15% by weight (or 1,500 ppm), to provide the desired anticaries efficacy. A wide variety of fluoride ion releasing materials can be employed as sources of water-soluble fluoride in the present invention including sodium fluoride, potassium fluoride, sodium monofluorophosphate and sodium hexafluorosilicate among others. Sodium monofluorophosphate and sodium fluoride are particularly preferred, as well as mixtures thereof.

CGMP Containing Dentifrice Component

The second, CGMP containing dentifrice component of the present invention, is maintained physically separate from the fluoride containing dentifrice component prior to use. The CGMP containing component has within its dentifrice vehicle a casein glycomacropeptide compound, such as those identified in U.S. Pat. No. 4,992,420 as kappa-caseino glycomacropeptides and desialyated derivatives thereof.

The term "kappa-caseino glycopeptides" includes within its meaning a caseino glycopeptide, which is the water-soluble component emanating from the hydrolysis of kappa-casein with rennin, and a caseino-glycopeptide obtained by proteolysis of caseino-macroglycopeptide. Desialylated derivatives are obtained from caseino glycopeptides by more or less complete elimination of the sialic acids, i.e. N-acetylneuraminic and N-glycollylneuraminic acids, from the oligosaccharide chains of the caseino glycopeptide.

The preparation of kappa-caseino-glycopeptides is more fully disclosed in U.S. Pat. No. 4,992,420, and U.S. Pat. No. 5,075,424 which are incorporated herein by reference. The method disclosed within U.S. Pat. No. 5,075,424 comprises adjusting the pH of a solution of milk starting materials (i.e. cheese whey), by the addition of an acid, such as hydrochloric, sulfuric, acetic, lactic, or citric acid; ultracentrafiltering the pH adjusted whey with a membrane having a molecular weight cut-off of 10,000 to 50,000; and collecting the filtrate which contains the desired kappa-caseinoglycopeptides.

The CGMP is incorporated in the oral composition of the present invention at a concentration of about 2 to about 15% by weight, and preferably at about 8 to about 12% by weight of the CGMP component.

As CGMP may be inactivated by the presence of anionic surfactants, to avoid any such biological inactivation of the CGMP by the surface active agent when anionic surfactants are used in the preparation of the CGMP containing dentifrice, a hydrolyzed protein compound is included in the dentifrice composition. Useful protein compounds include hydrolyzed collagen proteins, specifically positively charged hydrolyzates containing high concentrations of basic amino acids obtained by extraction from a partially hydrolyzed collagen faction and isolation by ion exchange treatment with an anion exchange resin or a partially charged hydrolyzed collagen protein. Such hydrolyzed collagen proteins are known to the art and are more fully described in U.S. Pat. No. 4,391,798. Commercially available hydrolyzed collagen proteins include Crotein Q®, a quaternary derivative of hydrolyzed collagen protein available commercially from Croda Inc., New York, N.Y. Crotein Q has a minimum pH of 9.5–10.5, is an off-white, free-flowing powder and its adopted name is steartrimonium hydrolyzed animal protein. Another example of a commercially available hydrolyzed collagen protein is gelatin (food grade) available from American Gelatin Company, a hydrolyzed collagen protein prepared by boiling animal parts such as skin, tendons, ligaments and bones with water.

The presence of about 0.1 to about 2.5% by weight of the hydrolyzed protein compound in the casein glycomacropeptide component of the oral composition of the present invention is sufficient to inhibit any biological inactivation of the casein glycomacropeptide caused by contact with the anionic surfactant.

As certain casein glycomacropeptide compounds are slightly acidic in nature and it is desired that the pH of each component of the dentifrice of the present invention be generally in a neutral range, preferably between pH 6.7 and pH 7.2, a basic buffering agent may be required. The preferred buffering agent is sodium hydroxide, which is added in a quantity to obtain the desired neutral pH.

An optional ingredient within the casein glycomacropeptide component of the dentifrice composition of the present invention is a preservative to prevent microbial growth within the component. Suitable preservatives include methylparaben, propylparaben, and benzoates such as sodium benzoate. The quantity of such preservatives generally is from about 0 to about 5%, preferably from about 0.1% to about 2% by weight of the component.

Other Ingredients Common to the Dentifrice Components

Inorganic or organic thickeners (i.e. polymeric binders) may be included in the components of the multicomponent dentifrice of the present invention. Organic thickeners include natural and synthetic gums and colloids such as carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners are preferred and include amorphous silica compounds which function as thickening agents such as, colloidal silica compounds available under tradenames such as Cab-o-sil fumed silica from Cabot Corporation and distributed by Lenape Chemical, Bound Brook, N.J., Zeodent 165 from J. M. Huber Chemicals Division, Havre de Grace, Md. 21078, and Sylox 15 from Grace Davidson, Baltimore, Md. 21203. Either inorganic or organic thickening agents, or combinations thereof, may be present in both components of the instant dentifrice in proportions of about 0.1 to about 5% by weight, preferably about 0.4 to about 2% in each of the two components of the instant dentifrice.

A striped dentifrice product may be obtained using the multicomponent dentifrice of the present invention, wherein colorants of contrasting colors are incorporated in each of the dentifrice components to be dispensed; the colorants being pharmacologically and physiologically nontoxic when used in the suggested amounts. Colorants used in the practice of the present invention include both pigments and dyes.

Pigments used in the practice of the present invention include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The concentration of the pigment or dye useful in each component of the dentifrice composition is from about 0 to about 2 percent by weight of the respective component and preferably from about 0.05 to about 0.5 percent by weight of the respective component.

Other ingredients which may be incorporated in the components of the present invention, include antibacterial agents, antitartar actives, sweeteners and/or flavors. Particularly preferred antibacterial agents are noncationic antibacterial agents based on phenolic and bisphenolic compounds, halogenated diphenyl ethers such as triclosan, benzoate esters and carbanilides. Such antibacterial agents can be present in quantities from about 0.03 to about 1% by weight of the particular component.

When noncationic antibacterial agents are included in any of the dentifrice components, there is also preferably included from about 0.05 to about 5% of an antibacterial enhancing agent (AEA) which enhances the delivery and retention of the noncationic antibacterial agent to, and retention thereof on oral surfaces. AEA's useful in the present invention are disclosed in U.S. Pat. Nos. 5,188,821 and 5,192,531; and include synthetic anionic polymeric polycarboxylates, in the form 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez, e.g. AN 139 (M.W. 500,000), AN 119 (M.W. 250,000) and preferably S-97 Pharmaceutical Grade (M.W. 700,000) available from ISP Technologies, Inc., Bound Brook, N.J. 08805.

Antitartar actives such as tetrapotassium or tetrasodium pyrophosphates can be present in concentrations from about 0.5 to about 8% by weight of the particular component. The sweetener will normally be that of an artificial or synthetic sweetener and the normal proportion thereof present will be in the range of 0.1 to 1% by weight of the respective component, preferably 0.2 to 0.5% by weight the respective component. The flavor content, which is preferably of a mixed peppermint/menthol flavor, will usually be in the range of 0.5 to 2% by weight of the respective component, preferably 0.5 to 1.0% by weight of the respective component. The contents of any other components or adjuvants will normally not exceed 10% by weight, often will be less than 5% by weight, and can be as low as 0%.

Preparation of the Dentifrice

To prepare the components of the present invention, generally the humectants e.g. glycerin, propylene glycol, polyethylene glycol ingredients, are dispersed with any sweetener and water in a conventional mixer, until the mixture becomes a homogeneous gel phase. Into the gel phase are added a pigment such as $TiO_2$, preservative such as sodium benzoate, any antibacterial agent such as triclosan, any antibacterial enhancing agent such as Gantrez, any tartar control agents such as tetrasodium pyrophosphate or sodium tripolyphosphate, any fluoride salt such as sodium fluoride, and/or casein glycomacropeptide anticaries agents. These ingredients are mixed until a homogenous phase is obtained. The pH of the resultant mix is then adjusted using a basic buffering solution such as a 50% solution of sodium hydroxide. Thereafter any hydrolyzed protein compound and the thickener, flavor and surfactant ingredients are separately added and dispersed into a final mix; the final mix is agitated at high speed under vacuum of from about 20 to 100 mm of Hg. The resultant product Is in each case a homogeneous, semi-solid, extrudable paste product.

Packaging of the Dentifrice

The multicomponent dentifrice composition of the present invention is packaged in a suitable dispensing container in which the components are maintained physically separated and from which the separated components may be dispensed synchronously as a ribbon for application to a toothbrush. Such containers are known in the art. An example of such a container is a two compartment dispensing container, such as a pump or tube, having collapsible sidewalls, as disclosed in U.S. Pat. Nos. 4,487,757 and 4,687,663; wherein, the container body is formed from a collapsible plastic web and is provided with a partition within the container body defining separate compartments in which the physically separated components are stored and from which they are dispensed through a suitable dispensing outlet.

The following example is further illustrative of the present invention, but it are understood that the invention is not limited thereto. All amounts and proportions referred to herein and the appended claims are by weight.

EXAMPLE

To determine the remineralization effect on teeth of a dentifrice containing the fluoride ion and casein glycomacropeptide component combination of the present invention, a two component composition of the present invention, designated Toothpaste I, was prepared. The ingredients of each of the two components of Toothpaste I are itemized in Table I, below.

TABLE I

Toothpaste I

| Ingredient | 1st Component (in weight %) | 2nd Component (in weight %) |
|---|---|---|
| Glycerine | 20.00 | 29.00 |
| Carboxymethyl Cellulose | 0.20 | 0.30 |
| Iota Carrageenan | 0.65 | 0.65 |
| Deionized Water | 47.29 | 43.314 |
| Sodium Saccharin | 0.25 | 0.25 |
| Sodium Benzoate | 0.30 | — |
| Sodium Hydroxide (50% sol'n) | 0.31 | |
| Hydrated Silica (Zeodent-115) | 18.00 | 24.00 |
| Sodium Lauryl Sulfate | 1.00 | 1.00 |
| Gelatin | 1.00 | — |
| Titanium Dioxide | 0.25 | 0.25 |

TABLE I-continued

Toothpaste I

| Ingredient | 1st Component (in weight %) | 2nd Component (in weight %) |
|---|---|---|
| Flavor | 0.75 | 0.75 |
| CGMP | 10.00 | — |
| Sodium Fluoride | — | 0.486* |
| Total | 100.00 | 100.00 |

*0.486 weight % is equivalent to 2200 ppm of fluoride ion concentration in the 2nd Component.

Toothpaste I, which contained 5% CGMP and 1100 ppm F, when the individual components stored in a dual compartmentalized container were extruded synchronously and combined immediately prior to use, was evaluated in vivo for remineralization efficacy using the surface microhardness methodology described in Zhang et al, Journal of Clinical Dentistry, 6:148–153 (1995). The study was conducted as a randomized, cross-over, double-blind study with 12 healthy adults. Enamel demineralization of bovine enamel blocks was achieved in vitro by covering the bovine enamel blocks with glucan containing *Streptococcus mutans* Ingbritt-1600 serotype C, which was then exposed to a 25% sucrose solution for 2 hours at 37° C. The adult subjects were fitted with oral maxillary palatal retainers, each holding four demineralized enamel blocks. The subjects brushed their teeth for 30 seconds with 1.5 grams of Toothpaste I, swished for an additional 60 seconds, rinsed with water and then retained the blocks intraorally for 4 hours. Percent mineral recovery for each enamel block was calculated as the ratio of the changes in enamel microhardness due to treatment (remineralization or remin.) and sucrose challenge (demineralization or demin.). As a control, the subjects were required to use as a normal daily oral hygiene practice during the study a one component placebo toothpaste, designated Toothpaste II, of the general formula of Toothpaste I, except that there was absent within Toothpaste II any fluoride ion or casein glycomacropeptide. The remineralization efficacy results for Toothpaste I and the placebo Toothpaste II are summarized in Table II, below.

For purposes of further comparison, the procedure of the Example was repeated using a commercially available fluoride toothpaste containing 1100 ppm NaF bearing the Acceptance by the Council on Dental Therapeutics of the American Dental Association (ADA) as being effective in preventing caries (designated Toothpaste III).

The remineralization results for Toothpaste III are also recorded in Table II below.

TABLE II

Remineralization Efficacy

| Toothpaste No. | Remin. (% Mineral Recovery) |
|---|---|
| I. (5% CGMP/1100 ppm F as NaF) | 29.90 ± 7.37 |
| II. (No F and No CGMP) | 1.70 ± 7.76 |
| III. (1100 ppm F as NaF) | 21.83 ± 8.76 |

The results as shown in Table II, above, are statistically each significantly different, to a statistical significance of $p<0.035$. The results recorded in Table II show that the remineralization efficacy of Toothpaste I is significantly better than that which contained no F or CGMP and is also significantly better, by almost 37%, than the ADA Accepted commercial anticaries Toothpaste III containing 1100 ppm F.

We claim:

1. A multicomponent anticaries dentifrice composition comprising, a first dentifrice component containing a dentifrice vehicle with a fluoride ion releasing compound therein, that is free of any casein glycomacropeptide compound and a second dentifrice component containing a dentifrice vehicle with a casein glycomacropeptide compound therein, that is free of any fluoride ion, the components being physically separate before use and when combined upon application to the teeth, providing enhanced enamel remineralization.

2. The multicomponent dentifrice composition of claim 1, wherein the fluoride ion compound is a water-soluble fluoride compound.

3. The multicomponent dentifrice composition of claim 2, wherein the water-soluble fluoride compound is sodium fluoride.

4. The multicomponent dentifrice composition of claim 1, wherein the casein glycomacropeptide compound is a kappa-caseino glycomacropeptide, a kappa-caseino glycopeptide or a desialyated derivative thereof.

5. The multicomponent dentifrice composition of claim 1, wherein the first fluoride ion compound containing dentifrice component, contains from about 0.025% to about 1% by weight of the fluoride ion compound.

6. The multicomponent dentifrice composition of claim 1, wherein the second casein glycomacropeptide compound containing dentifrice component, contains from about 2 to about 15% by weight of the casein glycomarcopeptide compound.

7. The multicomponent dentifrice composition of claim 1, wherein the second casein glycomacropeptide compound containing dentifrice component, contains from about 8 to about 12% by weight of the casein glycomarcopeptide compound.

8. A method of remineralizing demineralized portions of tooth structures comprising, preparing a multicomponent oral composition comprised of physically separated dentifrice components, having a first dentifrice component containing a dentifrice vehicle with a fluoride ion compound therein, that is free of any casein glycomacropeptide compound and a second dentifrice component containing a dentifrice vehicle with a casein glycomacropeptide compound therein, that is free of any fluoride ion; combining the dentifrice components and then applying the combined components to the demineralized portions of tooth structures, whereby such application provides substantially enhanced remineralization.

9. The method according to claim 8, wherein the fluoride ion compound is a water-soluble fluoride compound.

10. The method according to claim 9, wherein the water-soluble fluoride compound is sodium fluoride.

11. The method according to claim 8, wherein the casein glycomacropeptide compound is a kappa-caseino glycomacropeptide, a kappa-caseino glycopeptide or a desialyated derivative thereof.

12. The method according to claim 8, wherein the first fluoride ion compound containing dentifrice component, contains from about 0.025% to about 1% by weight of the fluoride ion compound.

13. The method according to claim 8, wherein the second casein glycomacropeptide compound containing dentifrice component, contains from about 2 to about 15% by weight of the casein glycomarcopeptide compound.

14. The method according to claim 8, wherein the second casein glycomacropeptide compound containing dentifrice component, contains from about 8 to about 12% by weight of the casein glycomarcopeptide compound.

* * * * *